United States Patent [19]

Mahieu et al.

[11] Patent Number: 4,859,460
[45] Date of Patent: Aug. 22, 1989

[54] METHOD FOR REINFORCEMENT OR PERMANENT DEFORMATION OF HAIR

[75] Inventors: Claude Mahieu, Paris; Christos Papantoniou, Montmorency, both of France

[73] Assignee: Société Anonyme dite L'Oreal, Paris, France

[21] Appl. No.: 119,336

[22] Filed: Nov. 10, 1987

[30] Foreign Application Priority Data

Nov. 21, 1986 [FR] France ................................. 86 16252

[51] Int. Cl.⁴ .......................... A61K 7/09; A61K 7/11; A45D 7/04
[52] U.S. Cl. ........................................ 424/72; 424/78; 132/203; 132/209; 8/127.51
[58] Field of Search .................... 424/72, 78; 132/203, 132/209; 8/127.51

[56] References Cited

U.S. PATENT DOCUMENTS 2,615,783 10/1952 Haefele et al. ..................... 424/72 X
2,739,033 3/1956 Lubs ..................................... 424/71

FOREIGN PATENT DOCUMENTS 2043077 3/1983 United Kingdom .

OTHER PUBLICATIONS

Biochemistry, vol. 16, No. 7, Apr. 5, 1977, pp. 1424–1430.
Manufacturing Chemist, vol. 57, No. 10, Oct. 1986, p. 92.

Primary Examiner—Ellis P. Robinson
Assistant Examiner—Susan S. Rucker
Attorney, Agent, or Firm—Oliff & Berridge

[57] ABSTRACT

A means of reinforcing and/or mechanically deforming human hair, comprising a first stage in which the hair undergoes the action of a reducing agent so as to break the disulfide linkages of the keracystine to form thiol groups, followed by the application in a second stage of a modifying agent encouraging the establishment of new chemical linkages to the thiol groups, characterized in that the aforesaid modifying agent is a polyhaloacetylated polymer whose halogen atom is capable of reacting with thiol groups.

7 Claims, No Drawings

METHOD FOR REINFORCEMENT OR PERMANENT DEFORMATION OF HAIR

The present invention concerns a new means of reinforcing and/or permanently deforming human hair and a formulation for the implementation of this means.

Various means of reinforcing human hair and maintaining it in a given shape are known, whereby the hair is impregnated with a polymer solution which, after drying, leaves a film which provides the hair with enhanced cohesion and resistance to losing the temporary shape given to it by means of the procedure known as hair setting, for example.

Polymers of this type exert a purely mechanical action by forming a flexible sheath around each hair, thus delaying a return to its natural shape.

The use of so-called restructuring agents is also known, such as certain menthylol derivatives which penetrate the hair fiber and become polymerized therein, thus providing the hair with enhanced rigidity.

A means called permanent hair deformation is also known, which is based on the combined effects of mechanical deformation and a chemical modification of the hair. More specifically, the hair is first subjected to an initial chemical modification whereby certain disulfide linkages of the keratin molecule are broken, thus transforming these disulfide groups to thiol groups, whereby the fiber is temporarily plasticized, that is to say, the hair made deformable but not elastic. The hair next undergoes forced mechanical deformation, such as being curled on rollers or smoothed and flattened, following which the hair undergoes a second chemical modification, especially consisting of reforming by means of oxidation disulfide bonds from thiol groups. As a result of the aforesaid forced deformation of the hair, new linkages are established at sites other than the original sites, which results in each strand of hair being set in the new imposed shape.

The purpose of the present invention is to provide a new means which has two effects: it enables the hair to be reinforced as well as being subjected to permanent deformation, if required. This permanent deformation may consist of curling or straightening the hair as well as uncrimping.

Just as in conventional cold permanent waving, the means according to the present invention comprises a hair reduction stage and, in the second stage, is characterized by the application of a polymer capable of forming covalent bonds are formed with the thiol groups of the chemically reduced hair. As a result, the polymer is chemically bound to the hair and acts as a reinforcing agent. Moreover, if the hair undergoes mechanical deformation at the same time as the polymer application, the hair will maintain the shape imposed on it in the course of the latter process.

Consequently, the means according to the present invention is of particular interest for the treatment of fine or sensitized hair which may have undergone degrading procedures, such as dyeing, for example.

Moreover, one of the advantages of using a polymer reagent is that such reagents are unable to penetrate the scalp and thus possible problems of toxicity do not arise.

Therefore, the purpose of the present invention is to provide a means of reinforcing and/or permanently deforming the hair, whereby, in an initial stage, the hair is first acted upon by a reducing agent so as to break the disulfide keratocystine linkages to form thiol groups, following which, in a second stage, a modifying agent is applied which promotes the formation of new chemical linkages with the thiol groups, characterized in that the aforesaid agent is a polyhaloacetylated polymer whose halogen component is capable of reacting with the thiol groups.

The first stage of the means according to the present invention, which consists of opening the S—S keratin linkages with a formulation containing a reducing agent, is a reaction which is known as such and the reducing agents which can be used for this purpose are well known to permanent wave experts.

By the same token, the formulation of reducing compounds suitable for the achievement of this first phase is known as well and has been described in the cosmetological literature, such as "Problemes capillaires" (Hair Problems) by E. Sidi and C. Zviak, Paris (1966), for example.

No attempt will be made to provide a detailed description here of the composition of reducing formulations of this type, since they do not form a part of the present invention. Generally speaking, these reducing compounds contain a reducing agent, such as a mercaptan, for example, an alkali metal or ammonium sulfite or bisulfite, thioglycolic acid, thiolactic acid or alternatively a thioglycolic or thioloactic acid ester (such as glycerol or glycol monothioglycolate, for example), whereby the pH of the latter formulation will generally lie in the 7–10 range and preferably in the 8–9.5 range. The reducing agent will preferably be present in the reducing formulation at a concentration of 2–25% by weight relative to the total weight of the aforesaid formulation.

Reduction levels in the 5–30% range can be obtained in the first stage of this method.

The basic pH of the aforesaid reducing formulations is generally obtained with the help of alkaline agents such as ammonia, monoethanolamine, diethanolamine, triethanolamine, and the like.

Particular embodiments of the means according to the present invention may possess the following characteristics, taken individually, or in combination:

The polyhaloacetylated polymer is allowed to act on the reduced hair for a period which may, for example, vary from 10–45 minutes; the means is preferably applied at a temperature of 25°–70° C.; the hair is then rinsed in water and dried, if desired;

The polyhaloacetylated polymer is allowed to act on the reduced hair which is stretched, either by being wound on rollers or smoothed and flattened by combing, for example and, after the polymer has acted for a sufficient period, the hair is rinsed and dried in a stretched condition; this method produces a permanent hair deformation, curling or straightening, as the case may be.

In a first variant of the present invention, the polyhaloacetyl polymer may, if desired, be applied in an admixture together with a conventional oxidant, such as hydrogen peroxide for example, or, according to a second variant, the hydrogen peroxide may be applied after the polyhaloacetyl polymer application, which method may be employed to complete the second stage of the means according to the present invention in cases where certain thiol groups may still remain.

The polyhaloacetylated polymers employed in the means according to the present invention are essentially characterized in that they all contain a halogen (chlorine or bromine but preferably the former), on a carbon at the alpha position relative to a carbonyl group.

These polyhaloactylated polymers, and preferably polychloracetylated polymers, can be obtained by various means:

A particular means of obtaining the aforesaid polymers is by the homopolymerization or copolymerization of a haloacetylated monomer carrying a polymerizable double bond; among the possible haloacetylated monomers, the following may be cited in particular: vinyl chloracetate, allyl chloracetate, N-allyl chloracetamide, methyl chloracetamido 2-acrylate, N-chloroacetamidomethyl acrylamide, N-chloroacetamidomethyl methacrylamide, 2-(chloroacetoxy)-propyl methacrylate, 2-(chloroacetylcarbamoyloxy)-propyl methacrylate, N-methacryloyl N'-chloroacetylurea, etc.; if copolymerization is employed, a copolymer will preferably be chosen which promotes favoring solubility of the final copolymer in the required solvent, which will generally be water or a water and alcohol mixture; among the suitable comonomers, the following may be cited in particular: N-vinyl pyrrolidone, N,N-dimethylacrylamide, N-acrylomidomethyl-2-oxopyrrolidone, 3-methacrylamidopropyl, 3-methacrylamidoproppyl-1 (N,N,N-trimethylammonium chloride, methacrylate, methylmethacrylate, N,N-dimethylacrylamide, etc., etc.

The haloacetylated monomers employed are known formulations and may be prepared by known methods:

The polyhaloacetylated polymers may also be obtained by attaching a haloacetylated group to a polymer-carrying amine or primary or secondary alcohol groups, whereby the haloacetyl group is attached in a known way (as described in the French document 1,149,161 or in the article by A. Carpov et al in Die Angew. Makromol. Chemie (Applied Makromolecular Chemistry), vol. 24, 1972, no. 322, pp. 101-120), for example, which consists of reacting a haloacetyl halide, preferable chloracetyl chloride with the aforesaid polymer carrying amine or alcohol groups; among the polymers which are suitable for this haloacetylation reaction, the following may be cited in particular: polyvinyl amine, polyvinyl alcohol, 2-hydroxyethyl polyacrylate, polylysine, copolymers obtained by condensing 2,2-dimethyl-1,3-diaminopropane with methylene-bisacrylamide, water-soluble protein hydrolysates, etc., etc.

The molecular weight of the polyhaloacetylated polymers employed according to the present invention will preferably lie in the 500–50,000 range.

Although certain of these homopolymers and copolymers are known, the following examples of preparation as well as a description of the preparation of haloacetylated monomers will be given below:

Among the homopolymers and polyhaloacetylated copolymers especially preferred in the implementation of the means according to the present invention, the following may be cited:

N-vinylpyrrolidone/vinyl chloroacetate copolymer
Methyl 2-chloroacetamidoacrylate/N-acrylamido-methyl-2-oxo-pyrrolidine copolymer
Methyl 2-chloroacetamidoacrylate homopolymer
N-chloroacetamidomethyl acrylamide/N-acrylamidomethyl-2-oxo-pyrrolidine copolymer
Methyl 2-chloroacetamidoacrylate/methylmethacrylamido-propyl trimethylammonium chloride copolymer
N-chloroacetamidomethyl acrylamide/methyl acrylate copolymer
N-chloroacetamidomethyl acrylamide homopolymer, and
N-chloroacetamidomethyl acrylamide/methacrylamidopropyl trimethylammonium chloride copolymer In the means according to the present invention, the polyhaloacetylated polymer is applied to the reduced hair, using a composition whose pH preferably lies in the 8-9.5 range, or alternatively, the hair may be first rinsed in a buffer solution whose pH lies in the above range.

The means according to the present means can be diagrammatically elucidated with the following chemical reactions:

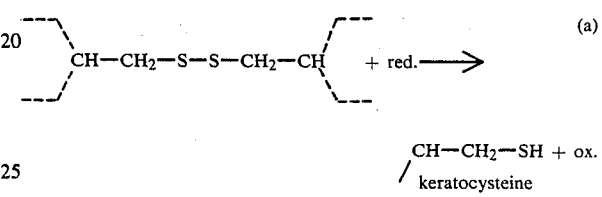

where red. and ox. respectively represent the reduced and oxided forms of an oxidation-reduction system, and

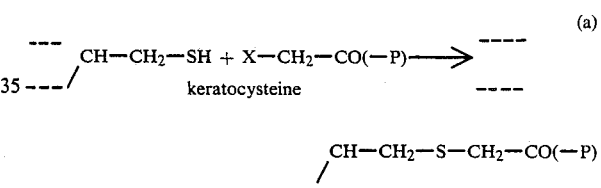

where X represents the halogen and (P) denotes the remaining polymer.

The present invention also concerns a formulation for implementing the means according to the above definition. This formulation is mainly characterized in that it includes at least one polyhaloacetylated polymer of the type defined above in a suitable vehicle.

In the formulation according to the present invention the polyhaloacetylated polymer is present in concentrations ranging from 0.5–10% by weight relative to the weight of the entire formulation.

Formulations according to the present invention may take the form of solutions of water or water and alcohol, whereby the alcohol takes the form of a lower alkanol such as ethanol or isopropanol, or alternatively, it may take the form of creams, gels, emulsions or aerosol sprays, etc.

Formulations according to the present invention may moreover include the usual common ingredients, such as pH modifiers, fragrances, colorants and dyestuffs, preserving agents, thickeners, surfactants or other cosmetic polymers, etc., etc.

The following examples will serve to exemplify the present invention in a nonlimitative fashion:

I. PREPARATION OF HALOACETYLATED MONOMERS

Example 1a

Preparation of methyl chloroacetamido 2-chloroacetamidoacrylate

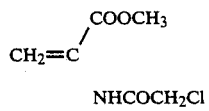

163.5 g of 2-chloroacetamidoacrylic acid prepared according to the procedure described by J. P. Greenstein in Arch. Biochem. 1947, vol. 14, p. 249 are added to a solution of 40 g of sodium hydroxide dissolved in 250 ml of water over a period of 1 hour, while the temperature is maintained at 10° C.; next, a solution of 170 g of silver nitrate in 1500 ml of water is then added. The white solid which forms is filtered, washed in water and then in acetone, dried and transferred to a reactor. 1000 g of methyl iodide and 1 g of hydroquinone monomethyl ether are then added and the mixture is refluxed for 2 hours. After filtration and concentration of the reaction mixture, 134 g of an oily product are obtained which will crystallize in a mixture of 130 ml of water and 220 ml of methanol (melting point: 42° C.).

Elemental analysis:

|     | Theoretical | Actual  |
| --- | ----------- | ------- |
| C   | 40.56%      | 40.69%  |
| H   | 4.51%       | 4.61%   |
| N   | 7.89%       | 7.68%   |
| O   | 27.04%      | 26.77%  |
| Cl  | 20.00%      | 20.13%  |

$^1$H RMN spectrum at 90 mHz in CHCl$_3$: —CH$_2$Cl d$\delta$=4.1 ppm

Example 1b

Preparation of N-chloroacetamidomethyl acrylamide

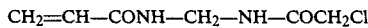

This product is prepared by reacting hydroxymethyl chloroacetamide with acrylamide in formic acid according to the method described by E. Mueller in Die Angew. Makr. Chem. (Applied Macro-chemistry), 1972, vol. 7, p. 99.

Example 1c

Preparation of 2-(chloroacetoxy) propyl methacrylate

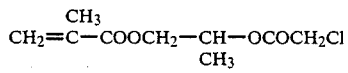

This product is prepared according to the reference cited in Example 1b, by reacting chloroacetic acid with 2-hydroxypropyl methacrylate.

Example 1d

Preparation of propyl 2-(chloroacetyl carbmoyloxy)propyl methacrylate

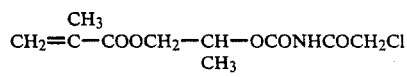

This product is obtained starting with chloromethylcarbonyl isocyanate and 2-hydroxypropyl methacrylate prepared according to the same reference in the literature as the previous example.

Example 1e

Preparation of N-methacryloyl-N'-chloro-acetylurea

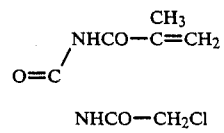

This product is prepared, starting with methacrylamide and chloromethylcarbonyl isocyanate according to the method described in the previous reference.

Example 2

Preparation of the N-acrylomidomethyl-2-oxopyrrolidine comonomer

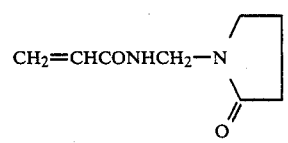

This monomer is synthesized according to the method proposed by B. Sebille, C.R. Acad. Sci., series C, 1969, vol. 269, p. 1513.

Example 3

Preparation of haloacetylated polymers by polymerization of haloacetylated monomers

Example 3a

N-vinyl pyrrolidone/vinyl chloroacetate copolymer 63.2 g of N-vinylpyrrolidone, 36.8 g of vinyl chloroacetate, 200 g of ethanol and 1 g of azobis-isobutyronitrile is placed in a reactor of 1000 ml capacity. The mixture is placed under a nitrogen blanket and is reflux-heated under constant stirring for 8 hours. The crude polymer solution is diluted in 200 g of acetone and precipitated in 5 l. of ethyl ether. After filtration and drying, a polymer is obtained which contains 37.5% of vinyl chloroacetate based on chlorine determination.

Example 3b

Methyl 2-chloracetamidoacrylate/N-acryloamidomethyl 2-oxopyrrolidine copolymer 93.8 g of methyl 2-chloracetamidoacrylate, 31.2 g of N-acrylamidomethyl-2-oxopyrrolidine, 3.5 l. of methanol and 50 g of a 33% hydrogen peroxide solution are placed in a 4 l. photochemical reactor equipped with a 2000 W type Q 2020 original Hanau-type lamp. The solution is heated to 50° C. and irradiated for 6 hours. The reaction mixture is then filtered and the solution is concentrated to 400 g and poured into 5 l. of ethyl ether. The resulting 93 g of polymer is then dried. The water-soluble fraction is extracted with 1.8 l. of water at 50° C. 68 g of water-soluble polymer are obtained.

Elemental analysis:

|   | Actual |
|---|---|
| C | 42.22% |
| H | 6.08% |
| N | 12.21% |
| O | 28.47% |
| Cl | 10.15% |

The above result indicates that the yield includes 54% of chlorinated monomer.

Example 3c

Methyl 2-chloroacetamidoacrylate homopolymer

The following ingredients are placed in a Hanovia-type photochemical reactor equipped with a medium pressure 100 W lamp supplied by Prolabo Inc:

25 g of methyl 2-chloroacetamidoacrylate
33.2 g of 33% hydrogen peroxide solution
610 g of methanol The solution is maintained at 20° C. and is irradiated for 8 hours. The reaction mixture is filtered, concentrated to 100 g and poured into 2 l. of ethyl ether under constant stirring; after filtration the resulting polymer is dried and the expected 4.3 g of polymer are in fact obtained.

Elemental analysis:

|   | Actual | Theoretical |
|---|---|---|
| C | 40.35% | 40.56% |
| H | 4.61 | 4.51 |
| N | 7.80 | 7.89 |
| O | 26.92 | 27.04 |
| Cl | 20.34 | 20.00 |

Example 3d

Methyl 2-chloroacetamidoacrylate/methylacryloamidopropyl trimethylammonium chloride copolymer (supplied by Texaco, USA under the trade name of Maptac)

The following constituants are placed in a tubular photochemical reactor equipped with a Hannovia 100 W medium pressure lamp:

4 g of methyl 2-chloroacetamidoacrylate
2 g of a 50% solution of Maptac in water
6.66 g of a 50% hydrogen peroxide solution
122 g of methanol The solution is maintained at 20° C. and is irradiated for 6 hours. The reaction mixture is filtered, concentrated to 15 g and precipitated in 500 ml of ethyl ether. A yield of 3.2 g of water-soluble polymer is obtained, characterized by a $^1$H RMN spectroscopy at 250 MHz (DMSO solvent).

Characteristic peak integration indicates that the yield contains 30% of chlorinated monomer.

Example 3e

N-chloroacetamidomethyl acrylamide/methyl acrylate copolymer 10 g of N-chloroacetamidomethyl acrylamide, 40 g of methyl acrylate, 400 g of a mixture of equal parts of water and ethanol and 0.25 g of azobis-iso-butyronitrile are placed in a reactor. The pH of the solution is adjusted to 2.5 with 0.1N hydrochloric acid and it is heated at 70° C. for 6 hours. After phase separation, the polymer is redissolved in 200 g of ethyl acetate and precipitated in 5 l. of hexane. After filtration and drying, 24 g of polymer is obtained which is soluble in a solution of 90 parts of ethanol and 10 parts of water.

Elemental analysis:

|   | Actual |
|---|---|
| C | 51.38% |
| H | 6.67 |
| N | 7.71 |
| O | 24.24 |
| Cl | 6.70 | which indicates that the yield contains 33% of chlorinated monomer.

Example 3f

N-chloroacetamidomethyl acrylamide homopolymer 2 g of N-chloroacetamidomethyl acrylamide, 8 g of absolute ethanol and 8 g of water are placed in a reactor; the pH of this solution is adjusted to 2.4 with 0.1M HCl; 0.1 g of azobis-iso-butronitrile is added and the mixture which is heated for 2 hours and the solvent refluxes. The polymer, which is soluble in the hot reaction medium, precipitates on cooling to 20° C. The precipitate is then recovered and dried.

Elemental analysis:

|   | Actual |
|---|---|
| C | 40.83% |
| H | 5.34 |
| N | 14.19 |
| O | 24.62 |
| Cl | 14.92 |

Example 3g

N-chloroacetamidomethyl acrylamide/methylacrylamidopropyl trimethylammonium chloride copolymer (Maptac)

144 g of N-chloroacetamidomethyl acrylamide, 72 g of a 50% solution of Maptac in water, 720 g of ethanol, 648 g of water and 9 g of azobis-iso-butyronitrile are placed in a reactor.

The mixture is heated with constant stirring under a nitrogen blanket for 4 hours until the solvent is refluxed; on completion of polymerization, the solvent is removed with a rotary evaporator until a syrup is obtained, which is precipitated in 10 l. of acetone. The solid residue is dried in an oven at 40° C. under reduced pressure. A yield of 180 g of pure polymer is obtained:

Elemental analysis:

|   | Actual |
|---|---|
| C | 42.2% |

-continued

| Actual | |
|---|---|
| H | 6.5 |
| N | 14.4 |
| O | 19.7 |
| Cl | 16.9 | which indicates that the yield includes 67.5% of the chlorinated monomer and 32.5% of Maptac.

Example 3h

N-chloroacetamidomethyl acrylamide/N-acrylamidomethyl-2-oxopyrrolidine copolymer 18 g of N-chloroacetamidomethyl acrylamide, 18 g of acrylamidomethyl 2-oxopyrrolidine, 144 g of ethanol, 144 g of water and 1.8 g of azobis-iso-butyronitrile are placed in a reactor. The mixture is heated under a nitrogen blanket for 2 hours with constant stirring.

After cooling, the mixture is concentrated to 110 g in a rotary evaporator and then diluted in 70 ml of acetone; the resulting solution is precipitated in 5 l. of acetone and the polymer is fitered and oven-dried under vacuum at 40° C.

Elemental analysis:

| Actual | |
|---|---|
| C | 47.8% |
| H | 6.5 |
| N | 15.2 |
| O | 21.4 |
| Cl | 8.9 | which indicates that the yield includes 50.4% of the chlorinated monomer and 49.6% of the comonomer.

Example 3i

N-chloroacetamidomethyl acrylamide/methacrylamidopropyl trimethylammonium chloride copolymer (Maptac)

80 g of N-chloroacetamidomethyl acrylamide, 40 g of a 50% solution of Maptac in water, 3 l. of methanol and a 50 g of a 33% hydrogen peroxide solution are placed in a 4 l photochemical reactor equipped with a 2000 W lamp (ref. Q 2020 original Hanau).

The solution is heated to 45° C. and irradiated for 4 hours. The reaction mixture is concentrated to 175 g and poured into 4 l. of acetone. The recovered polymer, which is completely water-soluble, is then dried.

Elemental analysis:

| Actual | |
|---|---|
| C | 41.45% |
| H | 6.10 |
| N | 21.85 |
| O | 13.23 |
| Cl | 16.82 | which indicates that the yield includes 63% of the chlorinated monomer and 37% of Maptac.

Example 3j

N-chloroacetamidomethyl acrylamide/N,N-dimethyl acrylamide copolymer 21 g of N-chloroacetamidomethyl acrylamide, 14 g of N,N-dimethyl acrylamide, 850 g of methanol and 42 ml of a 33% hydrogen peroxide solution are placed in a Hanovia-type photochemical reactor equipped with a 100 W medium pressure lamp.

The reaction solution is maintained at 20° C. and irradiated for 6 hours. The reaction mixture is then concentrated to 50 g and poured into 1 l. of diethyl ether. The recovered polymer, which is completely water-soluble, is then dried.

Elemental analysis:

| Actual | |
|---|---|
| C | 45.90% |
| H | 6.90 |
| N | 13.64 |
| O | 23.19 |
| Cl | 10.41 | which indicates that the yield includes 52% of the chlorinated monomer.

Example 3k

N-chloroacetamidomethyl acrylamide/methacrylaminopropyl trimethylammonium chloride copolymer (Maptac)

40 g of chloroacetamidomethyl acrylamide, 20 g of a 50% solution of Maptac in water, 15 g of a 33% hydrogen peroxide solution, 37.5 g of water and 100 g of isopropanol are placed in a reactor.

The solution is reflux heated and 40 ml of a solution of 5 g of ascorbic acid in 400 g of water is then added over a period of 40 min. The solvent is next reflux heated for a further four hours. The reactive mixture is next concentrated to one third of its orginal weight and the resulting polymer is precipitated in 3 l. of acetone. The polymer yield is dried under vacuum at 40° C.

Elemental analysis:

| Actual | |
|---|---|
| C | 42.38% |
| H | 6.35 |
| N | 14.02 |
| O | 21.97 |
| Cl | 15.43 | which indicates that the yield includes 74% of the chlorinated monomer and 26% of Maptac.

Example 3l

N-chloroacetamidomethyl acrylamide/propyl methacrylamidopropyl trimethylammonium chloride copolymer (Maptac)

28.8 g of chloroacetamidomethyl acrylamide, 14.4 g of a 50% solution of Maptac in water, 685 g of isopropanol, 3.6 g of azobis-iso-butyronitrile and 3.6 g of dodecylmercaptan are placed in a reactor.

The solvent is reflux heated for 16 hours. The polymer which partially precipitates on the walls of the reactor vessel and the precipitated polymer is dissolved in 100 ml of methanol.

The reaction mixture is concentrated and the resulting polymer is precipitated in 2 l. of acetone.

Elemental analysis:

| Actual | |
|---|---|
| C | 45.09% |
| H | 6.52 |
| N | 13.70 |
| O | 16.88 |
| Cl | 17.70 | which indicates that the yield includes 82% of the chlorinated monomer and 18% of Maptac.

Example 4

Preparation of a haloactylated polymer by binding a haloactylated halide to a polymer 6.4 g of polycondensate obtained by the polyaddition of 1.1-dimethyl-1,3-diaminopropane and methylenebisacrylamide according to the procedure described in French document 85.10,158, Example 2 are dissolved in 45 g of N-methyl pyrrolidone and heated to 50° C. 6 g of freshly distilled chloroactyl chloride are slowly added to the aolution. The reaction is completed in 10 hours. The resulting mixture is precipitated in 1 l. of acetone, the pH of the polymer recovered in an acqueous solution is adjusted to 9 with sodium bicarbonate, thus bringing about precipitation. The precipitate is then filtered, washed and dried. This process yields 5 g of polymer soluble in a 50/50 mixture of water and ethanol.

Elemental analysis:

| Actual | |
|---|---|
| C | 48.60% |
| H | 6.24 |
| N | 14.00 |
| O | 17.40 |
| Cl | 12.70 | which indicates that the yield includes 75% of the chlorinated monomer.

Example 5

Reaction of the polymer on reduced hair

Example 5a

Preparation of reduced hair

Natural hair is reduced in a 2% solution of thioglycol acid at a pH of 9.5 (ammoniacal buffer); this reaction takes 30 minutes at 30° C. Analysis of the hair indicates a reduction rate of 20-30% (ratio of cysteine content after reduction compared to the cystine content before reduction).

Example 5b

Method of reacting the polymer with the reduced hair

After reduction, the hair is immersed in a polymer solution whose pH has been adjusted to 9 (buffer consisting of 50 g of $NH_4Cl$, 900 ml of water, $NH_4OH$ d=0.92 to adjust pH to 9, water ad 1 l.) and which is maintained at 30° C. for 30 minutes; alternatively, the hair is first reduced and rinsed in a pH 9 buffer solution, impregnated in the polymer solution and maintained at 30° C. for a further 30 minutes. In both cases, the hair is subsequently rinsed and dried. In this example, after setting on rollers, the hair can be dried under a hood.

Example 5c

Determination of the chemical change to the hair after reacting with the polymer General method:

After the polymer treatment, the hair undergoes acid hydrolysis inside sealed tubes at 110° C.; the percentage of aminoacids on the hydrolysate is determined with a Technicon TSM auto-analyser. The cysteine which is reacted with the haloacetamide or the haloacetate group is transformed to S-carboxymethylcysteine according to the following scheme:

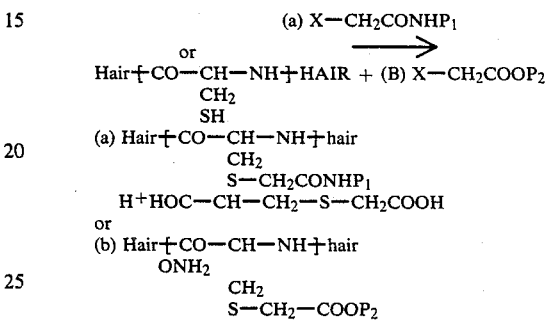

where X represents the halogen and $P_1$ and $P_2$ the remaining polymer.

Example 6

Examples of reduced hair treatment by polyhaloacetylated polymers

Example 6a

The polymer employed in Example 3c is dissolved in a 30:70 mixture of a pH 9 buffer and ethanol. Stoichiometric proportions of the cysteine present on the hair after reduction and the chloroacetamido polymer groups are employed. 10 ml of 0.9% polymer solution is prepared for the treatment of 300 mg of hair.

Depending on the rate of hair reduction, the reaction yield varies from 27 to 56%.

Example 6b

The polymer employed in Example 3b is reacted under the same conditions as in the previous example, except that in this case a 1.8% polymer solution is prepared in the ammoniacal buffer at pH 9. Reaction yields of 36-68% were obtained during various tests.

Example 6c

The polymer employed in Example 3d is reacted under the same conditions as in Example 5b. Reaction yields with the cysteine in the hair of 55-59% were obtained.

Example 6d

The polymer employed in Example 4 was dissolved to a concentration of 4.4% in a 33:66 pH 9 ammoniacal buffer:ethanol solution and reacted with the reduced hair (0.058 mole of cysteine per 100 g of hair). After 30 minutes of reaction at 30° C., a reaction yield of 43% was obtained.

Example 6e

The polymer employed in Example 3g was dissolved to a 2.45% in the the pH 9 ammoniacal buffer and reacted cysteine on the one hand and with the reduced hair on the other hand; after 30 minutes at 30° C., reaction yields of 98% and 65% respectively were obtained.

Example 6f

The polymer employed in Example 3h was dissolved in a 70:30 mixture of the pH ammoniacal buffer and ethanol and then reacted for 10 and 30 minutes with stoichiometric proportions of cysteine. Reaction yields of 89% and 98% respectively were obtained.

Example 6g

Example 6b was repeated except that in this case, the treatment was applied to a whole head of hair by impregnation. In this case, the rate of hair reduction by 0.3M thioglycol acid at pH 9 was 5% ($6.10^{-3}$ moles of cysteine present per 100 g of hair). After reacting with the polymer employed in example 3b, a sample of hair was taken and hydrolyzed. The S-carboxymethyl cysteine determination indicated a yield of 25–30% in this case.

Example 6h

The previous example was repeated except that the rate of reduction was raised to 12.5%.

After reacting with the polymer employed in example 3b, a reaction yield of 9% was obtained.

Example 6i

The polymer employed in this example was dissolved in the ammoniacal buffer at pH 9 and then reacted with reduced hair, whereby equimolecular quantities of the reactant groups were employed. After 30 minutes at 30° C., a reaction yield of 44% was obtained.

Example 6j

The polymer employed in this example was dissolved in the ammoniacal buffer at pH 9 and reacted with the reduced hair, whereby equimolecular quantities of the reactant groups were employed. After 30 minutes at 30° C., a reaction yield of 51% was obtained.

Conclusion

Generally speaking, after treatment of reduced hair by polyhaloactylated polymers according to the means proposed in the present invention, an enhancement of the cosmetic properties of the hair is observed. The following properties, in particular, display improvement:

Curl retention curls after winding around rollers; Easier disentanglement (the hair is easier to comb out) Furthermore, it is observed that hair treated according to this means possesses improved softness as well

Example 7

Some typical formulations

The following formulations can be used for the implementation of the means according to the present invention:

Lotions

| Polymer according to Example 3c | .90 g |
| --- | --- |
| Ethanol | 70.00 g |
| Fragrance | .05 g |
| Liquid ammonia ad pH 9 | |
| Water ad | 100.00 g |

In this example, the polymer according to example 3c may be substituted by the same quantity of the polymer according to example 3a.

Example 7b

| Polymer according to Example 3b | 1.80 g |
| --- | --- |
| Ethanol | 70.00 g |
| Fragrance | .02 g |
| Liquid ammonia ad pH 9 | |
| Water ad | 100.00 g |

In this example, the polymer according to example 3b may be substituted by the same quantity of the polymer according to example 3d.

Example 7c

| Polymer according to Example 4 | 4.40 g |
| --- | --- |
| Ethanol | 66.00 g |
| Fragrance | .04 g |
| Liquid ammonia ad pH 9 | |
| Water ad | 100.00 g |

Example 7d

| Polymer according to Example 3g | 2.45 g |
| --- | --- |
| Fragrance | .05 g |
| Liquid ammonia ad pH 9 | |
| Water ad | 100.00 g |

Example 7e

| Polymer according to Example 3h | 1.00 g |
| --- | --- |
| Ethanol | 33.0 g |
| Fragrance | .02 g |
| Liquid ammonia ad pH 9 | |
| Water ad | 100.00 g |

Gels

Example 7f

| Polymer according to Example 3i | 5.00 g |
| --- | --- |
| Hydroxymethylcellulose marketed by Hercules Inc., as "Natrosol HHR 250" | 3.00 g |
| Fragrance | .03 g |
| Liquid ammonia ad pH 9 | |
| Water ad | 100.00 g |

This gel is colorless and clear and has a viscosity of 2800 cP as measured with a Dragge Mobile spindle III apparatus.

Example 7g

| Polymer according to Example 3i | 3.00 g |
| --- | --- |
| Polyoxyethylenated nonylphenol (containing 9 moles of ethylene oxide) sold by GAF Inc., as "Antarox CO 630" | 5.00 g |
| Fragrance | .03 g |
| Liquid ammonia ad pH 9 | |

|                   |          |
|-------------------|----------|
| Distilled Water ad | 100.00 g |

85 g of this solution are packaged with 15% of an F114/F12 propellant mixture in proportions of 43:57 sold as "Freons" by the Du Pont de Nemours Corp.

These lotions, gels and aerosol foams are applied to hair which has first been chemically reduced, and which may or may not have been permanently deformed by mechanical means, for about 30 minutes at a temperature of about 30° C.

After removal of the mechanical means of deformation, where appropriate, followed by rinsing and drying, the hair is found to be soft to the touch and can be easily combed or brushed out.

Solution

Example 7h

| Polymer according to example 3k | 4 g  |
|---------------------------------|------|
| Propylene glycol                | 15 g |

For use, this solution in propylene glycol is mixed with 80 ml of water whose pH has been raised to 9 by the addition of ammonia. This solution is applied to hair which has first been chemically reduced and subject to mechanical deformation by means such as rollers. After 30 minutes the rollers are removed and the hair is rinsed. The resulting curls are soft and easily combed.

Powder

Example 7i 4 g of the polymer according to example 3k are packaged in the form of a powder. For use, the powder is dissolved in 96 g of water whose pH has been raised to 9 by the addition of ammonia. This solution is applied hair which has first been chemically reduced but not to mechanical deformation. After allowing the solution to act on the hair for about 30 minutes, the hair is rinsed in plain water. The hair is soft to the touch and can be easily combed out.

We claim:

1. A method for the reinforcement and/or permanent deformation of hair, comprising in a first step applying to hair a composition containing a reducing agent to form free thiol groups and in a second step applying to the hair a composition containing a modifying agent which promotes the formation of new chemical linkages with the thiol groups, the improvement comprising said modifying agent being a polyhaloacetylated polymer possessing halogen atoms which are capable of reacting with the free thiol groups.

2. The method of claim 1, wherein the composition containing the polyhaloacetylated polymer has a pH of about 8 to 9.5.

3. The method of claim 1 wherein the composition containing the polyhaloacetylated polymer is allowed to act on the hair for a period of 10 to 45 minutes at a temperature of 25° to 70° C.

4. The method of claim 1, wherein the composition containing the polyhaloacetylated polymer is allowed to act on hair which has first been chemically reduced and stretched.

5. A hair cosmetic composition to promote the formation of new chemical linkages with the free thiol groups of reduced keratin containing in an aqueous or hydralocoholic solution from 0.5 to 10% by weight of polyhaloacetylated polymer, said composition having a pH of about 8 to 9.5.

6. The hair cosmetic composition of claim 5 wherein the polyhaloacetylated polymer is polychloroacetylated homopolymer or copolymer.

7. The hair cosmetic composition of claim 5 wherein the polyhaloacetylated polymer has a molecular weight comprised from 500 to 50,000.

* * * * *